United States Patent [19]

Frigg et al.

[11] Patent Number: 4,803,976
[45] Date of Patent: Feb. 14, 1989

[54] SIGHTING INSTRUMENT

[75] Inventors: Robert Frigg, Bern; Paul Gisin, Waldenburg; Stephan M. Perren, Davos Dorf; Urs Jenny, Niederdorf; Gebhard Ritter, Mainz, all of Switzerland

[73] Assignee: Synthes, Paoli, Pa.

[21] Appl. No.: 183,490

[22] Filed: Apr. 8, 1988

Related U.S. Application Data

[63] Continuation of Ser. No. 852,576, Apr. 16, 1986, abandoned.

[30] Foreign Application Priority Data

Oct. 3, 1985 [CH] Switzerland ............... 4280/85

[51] Int. Cl.$^4$ .................. A61B 17/18; A61B 6/00
[52] U.S. Cl. ..................... 128/92 VD; 33/286; 378/205
[58] Field of Search ........... 128/92 R, 92 YZ, 92 YY, 128/92 V, 92 VD, 303 R; 33/262, 263, 286, 334; 378/162, 163, 205

[56] References Cited

U.S. PATENT DOCUMENTS

| 371,294 | 10/1887 | Woods | 33/334 |
|---|---|---|---|
| 2,407,845 | 9/1946 | Nemeyer | 33/286 |
| 2,490,648 | 12/1949 | Ohl | 33/286 |
| 2,502,171 | 3/1950 | Pashby | 33/334 |
| 2,650,588 | 9/1953 | Drew | 378/162 |
| 3,946,493 | 3/1976 | Torres | 33/263 |
| 4,078,869 | 3/1978 | Honeycutt | 33/286 |
| 4,222,175 | 9/1980 | Bernicky | 33/263 |
| 4,418,422 | 11/1983 | Richter et al. | 128/92 VD |
| 4,570,624 | 2/1986 | Wu | 128/92 VD |
| 4,625,718 | 12/1986 | Olerud et al. | 128/92 VD |

FOREIGN PATENT DOCUMENTS 3205404  9/1983  Fed. Rep. of Germany ........ 128/92 VD

OTHER PUBLICATIONS

David Seligson, M.D., "Concepts in Intramedullary Nailing", Copyright 1985, Grune and Stratton, Ltd.
Grosse and Kempf, "Dynamic Locking Nail System", Howmedica Catalog.

Primary Examiner—Stephen C. Pellegrino
Assistant Examiner—Ralph Lewis
Attorney, Agent, or Firm—Davis Hoxie Faithfull & Hapgood

[57] ABSTRACT

A sighting instrument, particularly for surgical purposes, comprising a handle, a tool socket and a direction finder which may be held between a radiation source and a radiation receiver, the position of which can be represented visibly by means of an image converter, allowing continuous adjustment of its orientation.

34 Claims, 6 Drawing Sheets

SIGHTING INSTRUMENT

This is a continuation of co-pending application Ser. No. 852,576, filed on Apr. 16, 1986, now abandoned.

FIELD OF THE INVENTION

The invention refers to a sighting instrument, particularly for surgical purposes.

BACKGROUND OF THE INVENTION

Certain surgical procedures require the use of a sighting device. For example, when an intramedullary nail is inserted in the medullary canal of a bone, it may be necessary to lock the end of the nail in place by inserting retaining pins, also called interlocking screws or studs, through interlocking holes at the distal end of the nail. It is important in inserting these studs that one should know the precise position of the interlocking holes in the nail to avoid unnecessary damage to the bone.

Devices are known in which a drill template is adjusted and ultimately fixed in the desired position by means of an x-ray image amplifier. For example, Swiss Pat. No. CH-A5 635 998 discloses an aiming device which has an aiming head with a hole for the insertion of a directional socket. The aiming head mounting is positioned in a holder that is connected to the x-ray machine and is suspended from the x-ray machine. This arrangement makes it difficult to position the apparatus and to fix it in position, with resulting unsatisfactory target precision. In addition, the stationary arrangement limits operation.

Because of these problems, an aiming device has been devised that can be used independently of the x-ray machine. Thus, German industrial design Pat. No. U1 84 17 428 describes a device with a receiving head that rests in a holder and is permeable to x-rays, and which accepts a drill bit or a drill wire. Even this improved device, however, has major disadvantages. In particular, the aiming process takes place during the drilling of the bone, which causes considerable darkening of the working field and low image resolution. Also, the lack of a drill housing to protect the patient's tissue leads to damage whenever the tool or instrument being used is changed.

In addition, all known devices suffer from a serious flaw in that it is impossible to verify the targeting procedure and to make the necessary corrections during the operation.

SUMMARY OF THE INVENTION

The present invention overcomes the drawbacks of the prior art devices described above by providing a sighting instrument which allows continuous control and correction of the position of the axis of the tool socket and provides for optimum protection of the tissue. The invention also permits considerably improved picture resolution to be achieved.

By means of the present invention, maximum precision can be achieved and the targeting process as a whole can be shortened, which is important for safety considerations in x-radiation work. For example, in a typical intramedullary nail locking procedure, the period of x-radiation can be reduced from a few minutes to ten seconds.

In accordance with the invention these results are obtained by means of a sighting instrument comprising a tool socket, a direction finder connected to said tool socket and a handle connected to said direction finder and tool socket, whereby the socket and direction finder may be maintained in a defined position relative to one another and may be held between a radiation source and a radiation receiver for adjusting the orientation of said direction finder and socket.

In another aspect the invention includes an apparatus for drilling a hole under conditions preventing direct observation of the direction of drilling which comprises a source of radiation, a receiver for receiving said radiation, a converter for visually displaying an object lying in the radiation field between said source and said receiver, and a sighting instrument comprising a drill socket, a direction finder connected to said drill socket and means for positioning said drill socket and direction finder in said radiation field whereby the direction of a drill bit inserted in said drill socket may be controlled by controlling the orientation of said direction finder.

In still another aspect the invention includes a method for drilling a hole in a bone for the insertion of a transverse retaining pin or stud in a transverse hole in an intramedullary nail which comprises positioning the bone in a radiation field so that the axis of the nail is transverse to the direction of the field and the axis of the transverse hole is aligned with the direction of the field, positioning a sighting instrument having a tool socket and a direction finder with an axis parallel to the axis of the tool socket, adjacent to the bone, so that the axis of the socket is aligned with the axis of the transverse hole, and drilling a hole in the bone, while controlling the direction of drilling by means of said direction finder.

The invention will be further described in the accompanying drawings, in which.

DETAILED DESCRIPTION

Figure 1:
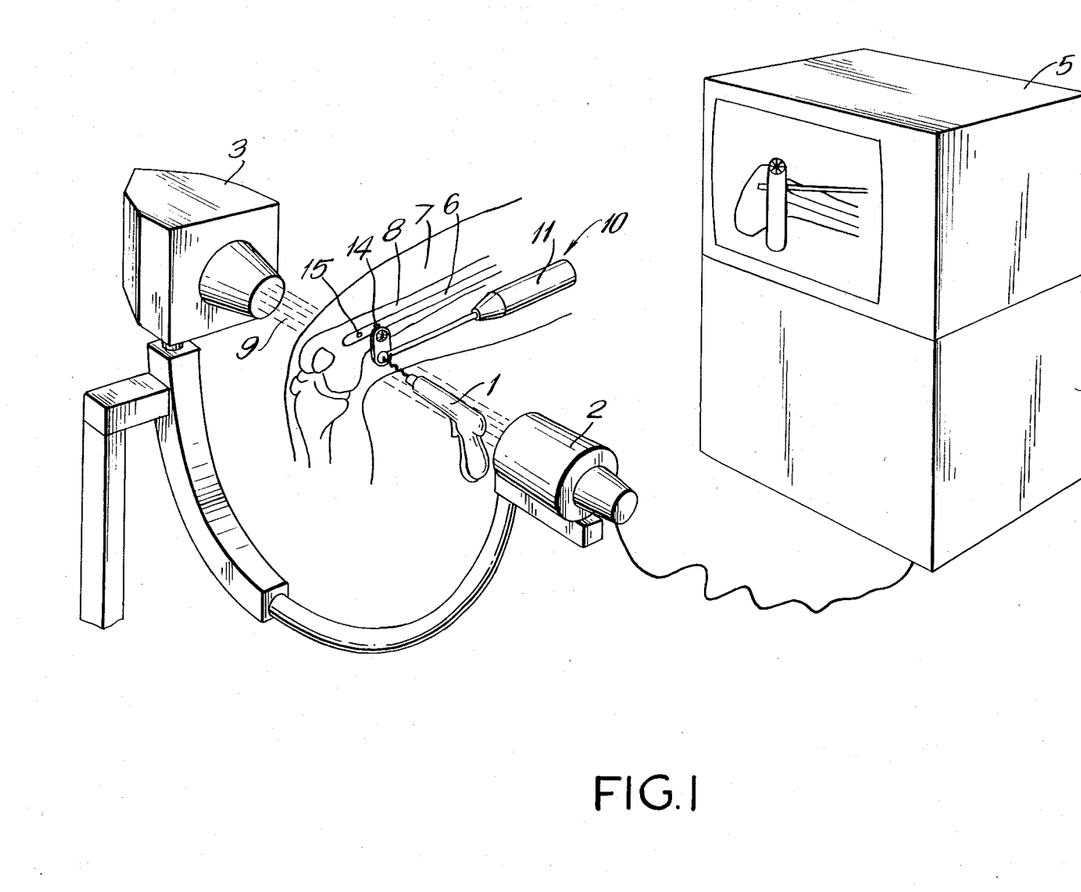
FIG. 1 is a view in perspective showing the sighting instrument according to the invention and associated x-ray equipment used in inserting retaining pins or locking studs in an intramedullary nail.

FIG. 1 shows a device according to the invention used for inserting retaining pins or studs in an intramedullary nail. As shown in FIG. 1 it is used in connection with an x-ray source 3, and x-ray receiver 2, and an image converter 4, having a monitor 5, connected to x-ray receiver 2.

In the radiation field 9 of the x-ray machine the patient's thigh 7 is shown positioned with an intramedullary nail 6 already inserted in the medulla of the femur 8. A sighting instrument 10 according to the invention is used with a tool 1, in this case an electric drilling device, to be used for drilling through the femur 8.

The position of the drill tip with regard to the nail 6 and the adjustment of the sighting instrument 10 in the radiation field 9 can be followed, and if necessary corrected, by observing its image on the monitor 5 of the image converter 4.

Figure 2:
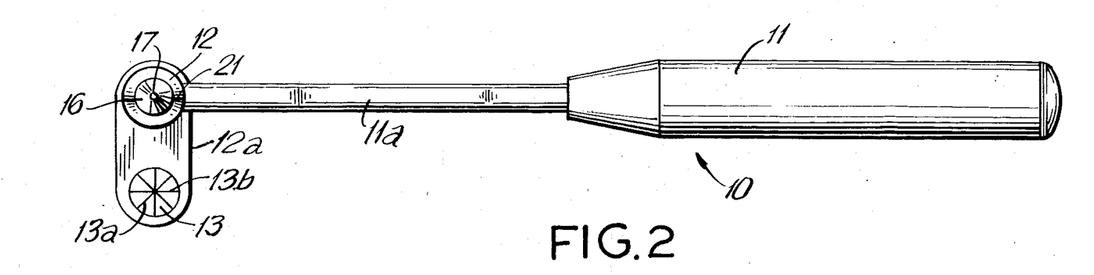
FIG. 2 is a plan view of a sighting instrument according to the invention.
Figure 3:
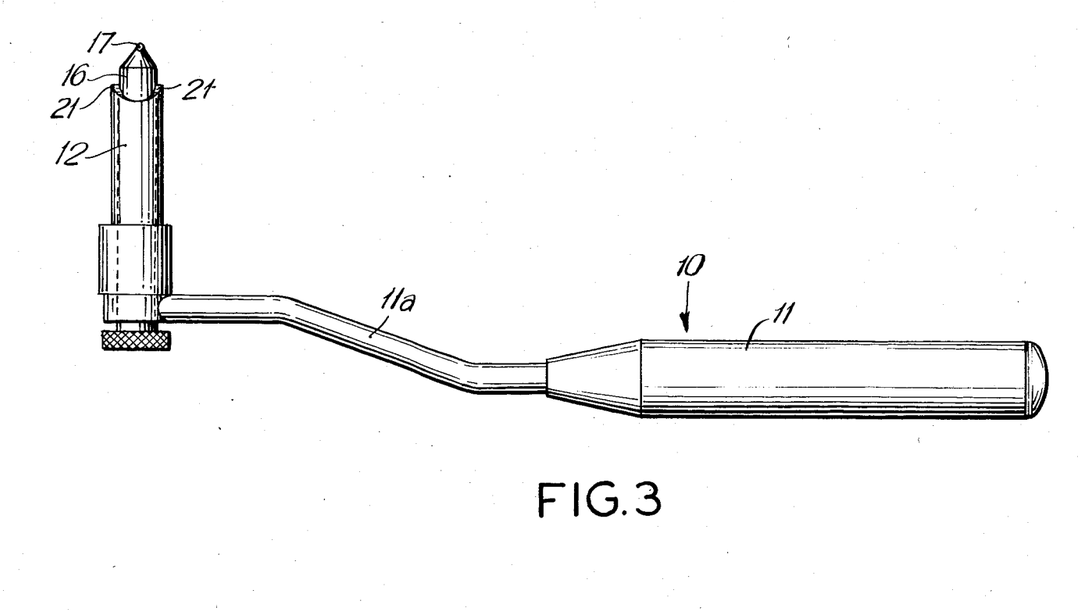
FIG. 3 is a side elevational view of a sighting instrument according to the invention with a pin inserted into the tool socket for determining the position point.

Referring to FIGS. 2 and 3 the sighting instrument 10 according to the invention consists of a handle 11 having an extended shank 11a to which a tool socket 12 is attached. A direction finder 13, having cross-hairs 13a, 13b is attached to the socket 12 by an arm 12a in such a way that it can be pivoted around tool socket 12, preferably with catches (not shown) that permit a 90° L pivot.

The tool socket 12 consists essentially of a hollow cylinder having two teeth 21. The cylinder is adapted to hold a pin 16 made of a radiation-permeable material, such as plastic, at the tip of which a reference component 17 is embedded. This reference component is made of a radiation-impermeable material, such as metal. In one embodiment of the invention, reference component 17 is spherical in shape.

Direction finder 13 is composed of two essentially parallel layers which are translucent or x-ray permeable with opaque aiming elements on both layers. For example, the direction finder 13 may consist of two sets of cross-hairs 13a, 13b angularly displaced 45° and lying opposite each other in different layers. Other appropriate aiming elements such as a circle and a dot may also be used.

Axis 20 of direction finder 13 and the axis 18 of tool socket 12 are co-planar. The distance between tool socket 12 and direction finder 13 is the same as the distance between the two interlocking holes, 14 and 15, of nail 6.

Figure 4:
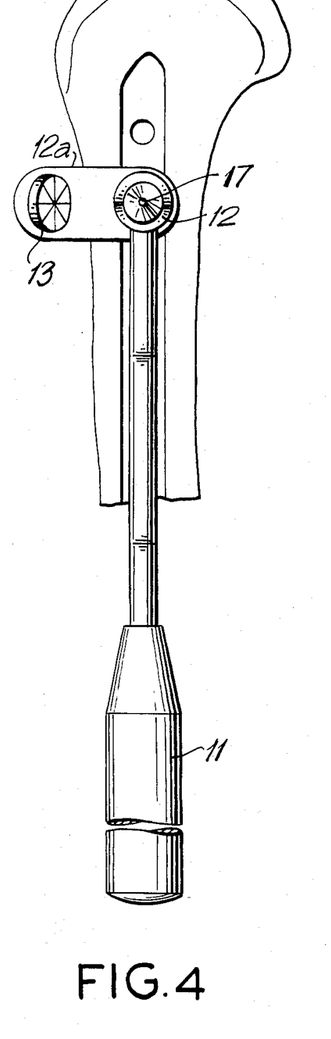
FIG. 4 is a plan view of the instrument according to the invention shown as in FIG. 3, in position but not yet aligned.
Figure 5:
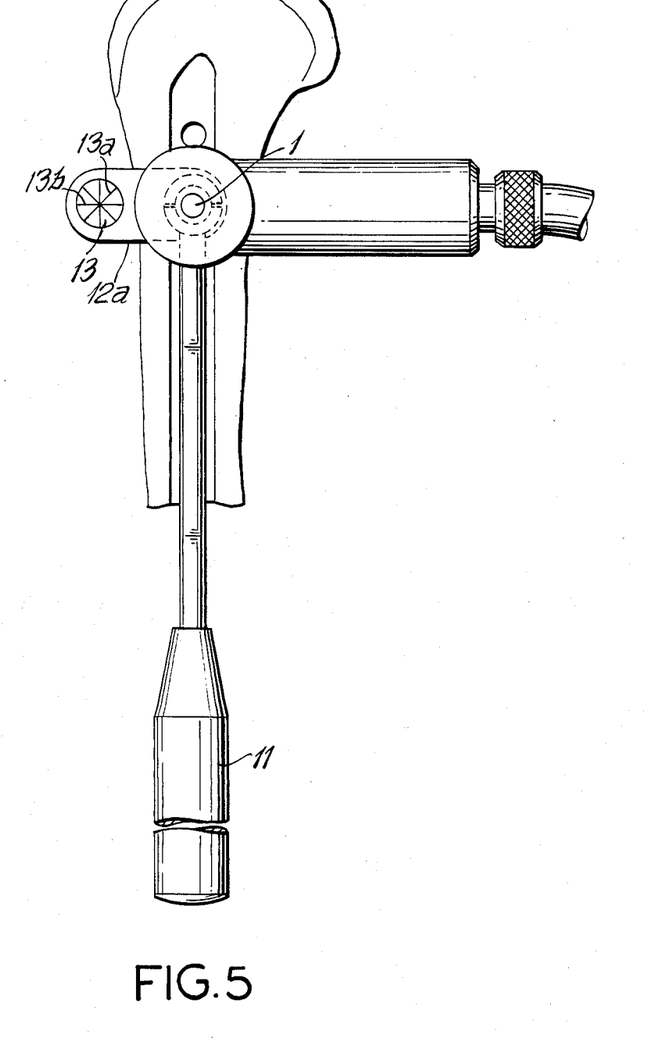
FIG. 5 is a plan view of a sighting instrument according to the invention in position and aligned in the radiation field, with a drill bit inserted in the tool socket.

The method of using the sighting instrument of the invention in an intramedullary nail locking procedure is shown in FIGS. 1, 4 and 5.

Before the sighting instrument 10 according to the invention is used, the relative position of the nail 6 in relation to the x-ray device 2 and 3 is adjusted in such manner that the interlocking holes 14 and 15 appear on monitor 5 to be round. This happens when the axes of interlocking holes 14 and 15 lie parallel to radiation field 9. The interlocking hole which is to be pinned should then lie in the center of the lower picture edge, so that the cross-hairs of direction finder 13 stand in the center of the image. The thigh 7 is covered with a shield (not shown) to protect it from the x-rays. The shield has an opening corresponding to the area to be observed. The radiation field must be within this opening.

Using the image converter for guidance, a cut is made through the skin lying exactly above the interlocking hole after which the tool socket 12 into which pin 16 has been inserted, can be driven through the cut (FIG. 4).

Pin 16 simplifies the introduction of the instrument through the soft portions of the patient's tissue, because of its spherical tip. After the insertion process has been completed, the tip of pin 16 with spherical reference component 17 is positioned over the center of the interlocking hole 14. This step is depicted in FIG. 4, and shows reference component 17 lying exactly in the center of tool socket 12. The position of the component 17 can be observed in the image converter because the pin 16 is permeable to x-rays while the component 17 is not.

The direction finder 13 is not used at this time. When the reference component 17 lies precisely in the center of the interlocking hole, the sighting instrument is pressed firmly against femur 8, for example by tapping it with a hammer. Pin 16 as shown in FIG. 3 is not clamped into tool socket 12 but is easily slidable within the socket. During the surgical procedure the sighting instrument is inserted into the patient's body with pin 16 projecting past teeth 21 as shown in FIG. 3. Its position is held by the surgeon's thumb, allowing gentle displacement of the soft tissues lying over the bone. When reference component 17 of pin 16 is placed at the desired location on the bone and tool socket 12 is pressed firmly against the bone, pin 16 is retracted in the socket. The teeth 21 of tool socket 12 prevent the sighting instrument 10 from slipping off the femur 8. In this stage of the operation, care should be taken that the sighting instrument 10 is not turned around the tool socket 12, since the tool socket 12, which serves as protection for the patient's tissue, contacts femur 8 with the two teeth, not with a central point.

After the sighting instrument 10 is positioned, the pin 16 is removed and a drill bushing, e.g., a 4.5 mm bushing, is inserted into the tool socket 12. A drill bit is now inserted into this drill bushing, the tip of the bit lying precisely over the center of the interlocking hole. The drilling direction is checked on the monitor and image converter and may be adjusted using the direction finder 13 to keep the drill aligned. This step is shown in FIG. 5, in which the direction finder 13 is positioned at right angles to the radiation field 9. Now the near cortex of the femur can be drilled into with the 4.5 mm drill bit. The drilling direction can be checked continuously with the image converter 4 and monitor 5. If necessary, the drilling direction can be corrected to maintain the correct sighting image.

As can be seen in FIG. 5, the interlocking hole is covered by the drill during this step in the operation and direction is maintained using direction finder 13. After drilling the near cortex the 4.5 mm drill bit is removed from the 4.5 mm drill bushing, and a 3.2 mm headed drill bushing is inserted as far as the far cortex. The image converter 4 can now be swung away and the far cortex can be drilled with the 3.2 mm drill bit. After the 3.2 mm headed drill bushing is removed, the required stud length is measured with a depth gauge, a thread is cut in the far cortex, and the locking stud is positioned. The sighting instrument may now be removed. For the insertion of the second locking stud the entire procedure described is repeated for the second interlocking hole.

Depending on the particular embodiment, radiation source 3 may emit radiation other than x-rays, such as ultra-sound waves. For training purposes, it may be desirable to use a radiation source 3 that emits visible light and a radiation receiver 2 that comprises a video camera.

The instrument 1 used with the sighting instrument according to the invention can be a saw, a syringe, or another surgical instrument instead of the drill described above. Although the sighting instrument according to the invention is appropriate for the surgical instruments and tools used in orthopedics, arthroscopy, spinal-column surgery, and tapping, the apparatus and method of the invention can also be used for non-surgical purposes.

Figure 6:
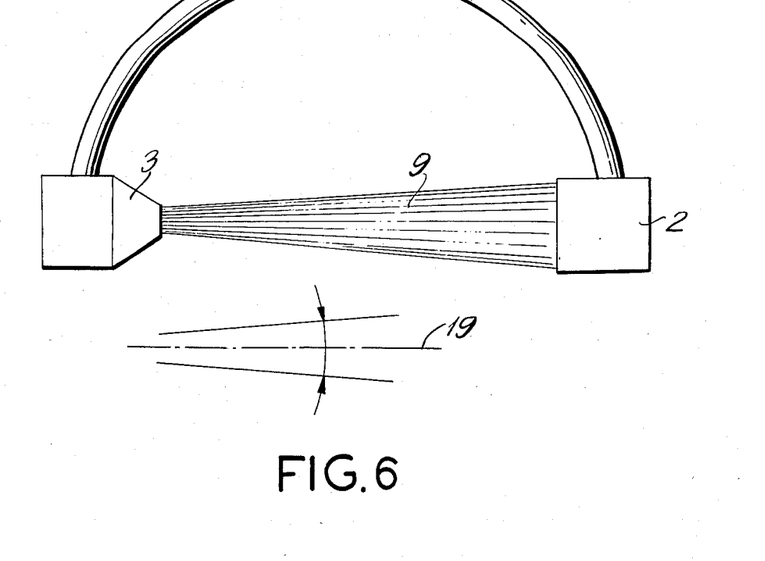
FIG. 6 is a schematic representation of the radiation field.
Figure 7:
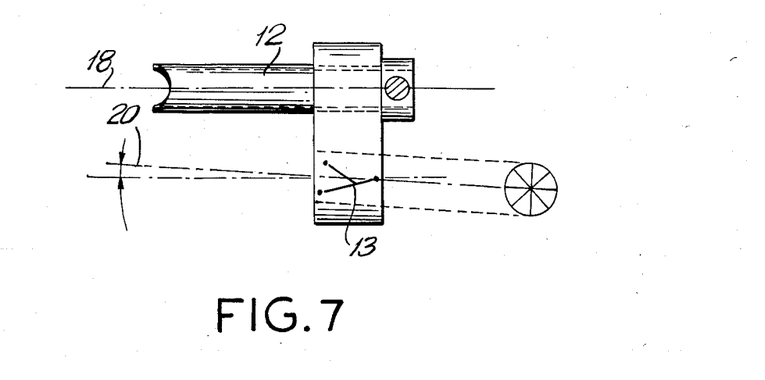
FIG. 7 is a cross-section through the tool socket and the direction finder of a modified form of a sighting instrument according to the invention.

FIG. 7 shows a way to increase the precision of the sighting instrument 10. The axis 18 of tool socket 12 which lies in a common plane with axis 20 of direction finder 13, can be at an angle to it, in order to take into account the divergence 19 of the radiation field 9 (FIG. 6). This embodiment, which improves the precision of the sighting instrument, can be constructed in either fixed or adjustable fashion.

Figure 8:
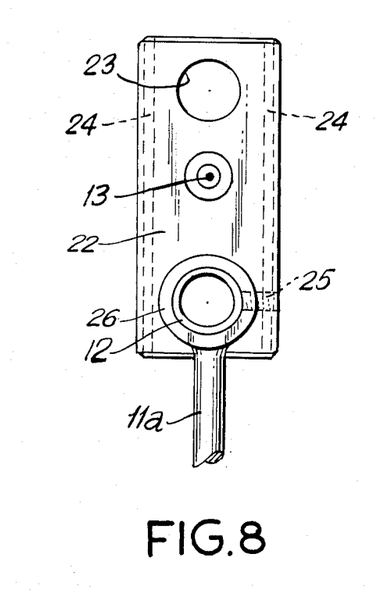
FIG. 8 is a plan view of a sighting instrument according to the invention with an additional drill bushing for inserting the second interlocking screw.
Figure 9:
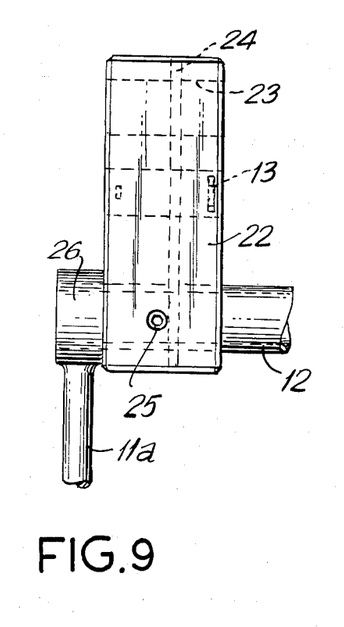
FIG. 9 is an elevational view seen from the right side of FIG. 8.
Figure 10:
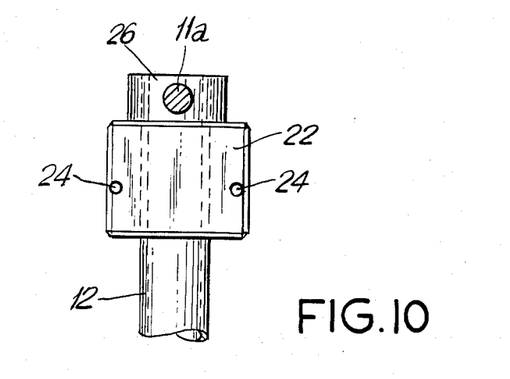
FIG. 10 is an end elevational view of the device of FIG. 8.

A further improved embodiment of the sighting instrument according to the invention is represented in FIGS. 8 to 11. FIGS. 8 to 10 show the construction of this embodiment, which further simplifies the insertion of the second interlocking screw. The unit 22, a rectangular block, is pivotably mounted on the tool socket 12 by means of a collar 26, fixed to the block 22. The block 22 may be fixed to the socket 12 by means of the set screw 25. The block 22 comprises beside the direction finder 13 a drill bushing 23 for insertion of a second interlocking screw. The distance between the centers of the drill bushing 23 and tool socket 12 corresponds exactly to the distance between the centers of the two interlocking holes 14, 15 of nail 6 and the axis of the bushing 23 is parallel to the axis of the socket 12.

The direction finder 13 is arranged between the drill bushing 23 and the tool socket 12, which is otherwise constructed identically to the previously described embodiment of the invention.

The unit 22 is made from a radiation-permeable material, such as plastic, and to aid in aligning unit 22 parallel to the radiation field 9 of the x-ray device 2 and 3, has two radiation-impermeable metallic wires 24 lying in a plane parallel to the plane of the drawing, and normal to the axes of the socket 12 and bushing 23.

Figure 11:
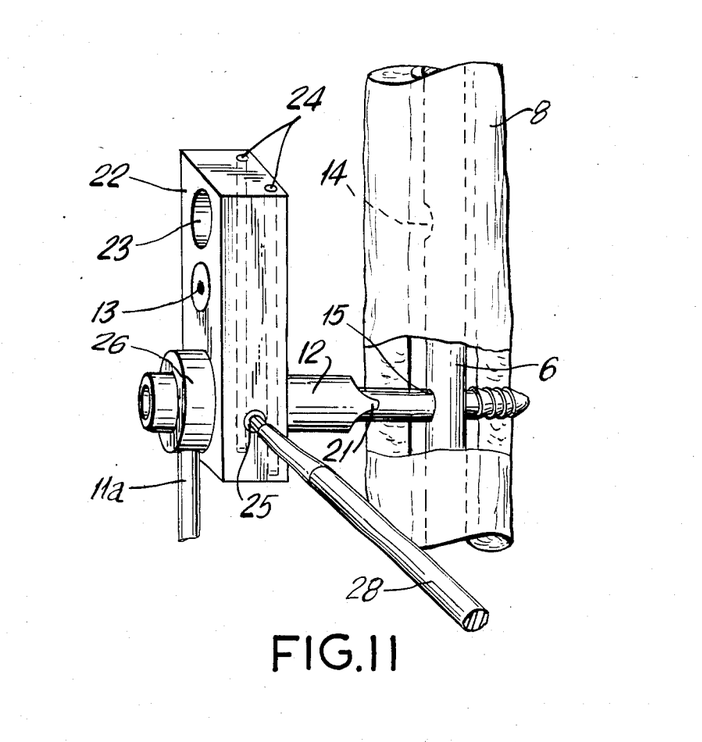
FIG. 11 is a perspective view of the sighting instrument according to FIGS. 8 to 10 with an inserted first interlocking screw.
Figure 12:
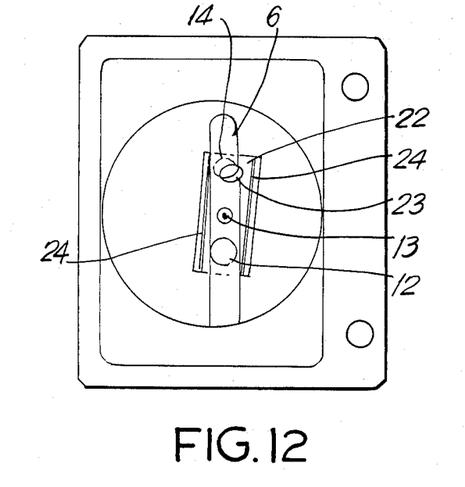
FIG. 12 is a monitor image of the sighting instrument according to FIG. 11 in a non-aligned position.
Figure 13:
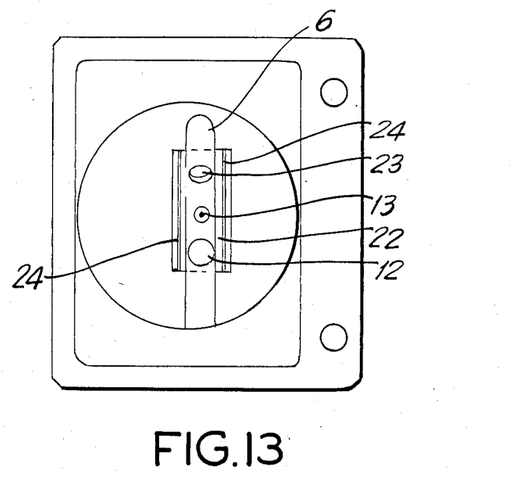
FIG. 13 is a monitor image of the sighting instrument according to FIG. 11 in an aligned position.

The technical procedure for insertion of the second interlocking screw by means of this improved embodiment of the invention is shown in FIGS. 11 to 13.

FIG. 11 shows the sighting instrument of FIGS. 8–10 after insertion of the first interlocking screw according to the surgical technique already described. The corresponding monitor image shows typically an arrangement as represented in FIG. 12, i.e., the metallic wires 24 embedded in the unit 22 are not yet aligned parallel to nail 6 but are at an angle to it. Accordingly the images of the drill bushing 23 and of the second interlocking hole 14 are not superimposed. Even though the plastic unit 22 is essentially radiation-permeable, in practice its contour is feebly visible on the monitor.

The surgeon then pivots unit 22 around the tool socket 12, which is firmly connected to the bone 8, until he has aligned the reference metallic wires 24 parallel to nail 6 on the monitor image and fixes unit 22 in this position by fastening the set screw 25.

The set screw 25 has a hexagonal socket in its head and the fixation of the unit 22 is accomplished by means of an ordinary hexagonal key 28 which is inserted into the socket of the fixation screw 25, as shown in FIG. 11.

Due to the divergence 19 of the radiation field 9 (FIG. 6), the drill bushing 23, and the second interlocking hole 14 do not appear circular, but elliptical, on the monitor. This circumstance, however, is not relevant for the alignment of unit 22, because the only condition to be observed is the parallel alignment of the reference wires 24 with nail 6.

After fixation of unit 22 by means of the set screw 25 the surgeon can release his hold on the handle 11 of the sighting instrument 10 and use both hands for inserting the second interlocking screw. For this purpose a tissue protecting bushing (not shown in the drawing) is inserted first into the drill bushing 23, into which the 4.5 mm bushing may then be inserted. Further procedures correspond to those described for the insertion of the first interlocking screw.

By means of this time-saving and precision-increasing embodiment of the invention it is possible to further reduce the already diminished x-ray dose by about 50%.

What is claimed is:

1. A sighting instrument for use in bone surgery for drilling holes in bones comprising a tool socket structured to receive drill guides for drills of varying diameter, a direction finder connected to said socket and having an axis at a predetermined angle to the axis of the tool socket for indicating the axial alignment of the tool socket and an elongated handle connected to said direction finder and tool socket whereby the socket and direction finder may be held in a predetermined orientation between a radiation source and a radiation receiver.

2. A sighting instrument according to claim 1 wherein the direction finder has an axis which is parallel to the axis of the tool socket.

3. A sighting instrument according to claim 1, wherein the axis of the direction finder is at an acute angle to the axis of the tool socket.

4. A sighting instrument according to claim 1 further comprising a pin made of radiation-permeable material for insertion into the tool socket, said pin having a reference component made of radiation-impermeable material.

5. A sighting instrument according to claim 4 wherein the reference component is spherical.

6. A sighting instrument according to claim 1, wherein the direction finder is pivotable around the tool socket.

7. A sighting instrument according to claim 6, wherein the direction finder is arranged in a unit pivotable around the tool socket, said unit further comprising a drill bushing having an axis parallel to the axis of the tool socket.

8. A sighting instrument according to claim 7, wherein the direction finder is arranged between the drill bushing and the tool socket.

9. A sighting instrument according to claim 1, wherein the direction finder comprises two aiming elements lying in different planes.

10. The instrument claimed in claim 1 wherein the tool socket is elongated to shield soft tissue from contact with a drill operating through said socket.

11. A sighting instrument comprising a tool socket, a direction finder connected to said tool socket and mounted in a unit pivotable around the tool socket for indicating the axial alignment of the tool socket, and a handle connected to said direction finder and a tool socket, whereby the socket and direction finder may be maintained in a defined position relative to one another and can be held between a radiation source and a radiation receiver and the orientation of said direction finder and socket adjusted, said unit further comprising a drill bushing having an axis parallel to the axis of the tool socket, said unit being made of radiation-permeable material and comprising radiation-impermeable reference means.

12. The sighting instrument claimed in claim 11 wherein the reference means comprises two parallel elongated elements, defining a plane generally normal to the plane defined by the axes of the tool socket and the bushing.

13. A sighting instrument for drilling holes through a bone for the insertion of two retaining pins in transverse interlocking holes in an intramedullary nail comprising a tool socket structured to receive drill guides for drills of varying diameter, a direction finder connected to the tool socket for indicating the axial adjustment of the tool socket and an elongated handle connected to said direction finder and tool socket, whereby the socket and direction finder can be held between a radiation source and a radiation receiver for adjusting the orientation of said direction finder and socket, the distance between the axes of said direction finder and socket being the same as the distance between the interlocking holes in said nail.

14. The instrument claimed in claim 13 and wherein the socket comprises a plurality of teeth for engagement with the bone to prevent slippage of the socket on the bone.

15. A sighting instrument for drilling holes through a bone for insertion of two retaining pins in transverse interlocking holes in an intramedullary nail comprising a block having a tool socket rotatably mounted in and extending through said block, a drill bushing in said block, the axis of said bushing being parallel to the axis of said socket and spaced from said socket at a distance equal to the distance between the holes in the nail, and a direction finder in said block and extending through said block for indicating the axial adjustment of the tool socket.

16. The instrument claimed in claim 15 wherein the direction finder is between the socket and the bushing.

17. A sighting instrument for drilling holes through a bone for insertion of two retaining pins in transverse interlocking holes in an intramedullary nail comprising a block having a tool socket rotatably mounted in and extending through said block, a drill bushing in said block, the axis of said bushing being parallel to the axis of said socket and spaced from said socket at a distance equal to the distance between the holes in the nail, and a direction finder in said block and extending through said block for indicating the axial alignment of the tool socket, said block being made of radiation permeable material and comprising radiation impermeable reference means.

18. The instrument claimed in claim 17 wherein the reference means comprises two parallel elongated elements arranged in a plane normal to the axes of said socket and bushing.

19. An apparatus for drilling a hole under conditions preventing direct observation of the direction of drilling which comprises a source of radiation, a receiver for receiving said radiation, a converter for visually displaying objects lying in the radiation field between said source and said receiver and a sighting instrument comprising a drill socket structured to receive drill guides for drills of varying diameter, a direction finder connected to said drill socket for indicating the axial orientation of the drill socket, the axis of said direction finder being parallel to the axis of the socket, and means for positioning said drill socket and direction finder in said radiation field, whereby the direction of a plurality of drills of different sizes inserted serially in said drill socket may be controlled by controlling the orientation of said direction finder.

20. The apparatus claimed in claim 19 wherein the radiation source is a source of x-radiation.

21. The apparatus claimed in claim 19, wherein the radiation source is a source of visible light and the radiation receiver is a video camera.

22. The apparatus claimed in claim 19 wherein the direction finder has two aiming elements located in different planes.

23. The apparatus claimed in claim 19 and comprising a pin for insertion into the socket for positioning the socket at the desired location for drilling.

24. The apparatus claimed in claim 23 wherein the pin is made of radiation permeable material except for a reference component made of radiation impermeable material.

25. A method for drilling a hole in a bone for the insertion of a transverse retaining pin in a transverse hole in an intramedullary nail which comprises positioning the bone in a radiation field so that the axis of the nail is transverse to the direction of the field and the axis of the transverse hole is aligned with the direction of the field, positioning a sighting instrument having a tool socket adapted to receive drill guides for drills of varying diameter and a direction finder with an axis parallel to the axis of the socket for indicating the axial alignment of the tool socket, adjacent to the bone so that the axis of the socket is aligned with the axis of the transverse hole, and drilling a hole in the bone using a plurality of drills of different sizes, while controlling the direction of drilling by means of said direction finder.

26. The method claimed in claim 25 wherein the direction finder has two aiming elements in different planes and the direction of drilling is maintained by keeping said elements aligned with one another.

27. The method claimed in claim 25 wherein said nail has two parallel transverse holes and the distance between the axis of the socket and the axis of the direction finder is equal to the distance between the axes of the transverse holes.

28. The method claimed in claim 25 wherein the position of the direction finder during drilling is observed by viewing the alignment of the aiming element on a image converter responsive to said radiation.

29. A method for drilling a hole in a bone for the insertion of a transverse retaining pin in a transverse hole in an intramedullary nail which comprises positioning the bone in a radiation field so that the axis of the nail is transverse to the direction of the field and the axis of the transverse hole is aligned with the direction of the field, positioning a sighting instrument having a tool socket and a direction finder with an axis parallel to the axis of the tool socket for indicating the axial alignment of the tool socket adjacent to the bone, inserting a pin having a body transparent to x-radiation and a tip impermeable to x-radiation through said socket and aligning said socket with the axis of the transverse hole by means of said pin, removing the pin and drilling a hole in the bone, while controlling the direction of drilling by means of said direction finder.

30. A method for drilling a hole in a bone for the insertion of a transverse retaining pin in a transverse hole in an intramedullary nail which comprises positioning the bone in a radiation field so that the axis of the nail is transverse to the direction of the field and the axis of the transverse hole is aligned with the direction of the field, positioning a sighting instrument having a tool socket and a direction finder with an axis parallel to the axis of the tool socket for indicating the axial alignment of the tool socket, adjacent to the bone so that the axis of the socket is aligned with the axis of the transverse hole, and drilling a hole in the bone, while controlling the direction of drilling by means of said direction finder, wherein the socket is kept aligned with the axis of one hole during drilling by maintaining the axis of the direction finder aligned with the axis of the second hole.

31. A sighting instrument for use in bone surgery in drilling holes in bones comprising a block, an elongated handle attached to said block, a tool socket in said block structured to receive drill guides for drills of varying diameter, and a direction finder comprising an aperture in said block having an axis with a predetermined relation to the axis of said tool socket for indicating the axial alignment of the tool socket, whereby said tool socket may be held between a source of radiation and a radiation receiver and positioned and maintained in a desired axial orientation.

32. The instrument claimed in claim 31 wherein the tool socket extends beyond the block to shield soft tissue from contact with drills operating through said socket.

33. The instrument claimed in claim 32 and comprising means on said socket for temporarily engaging a bone.

34. A sighting instrument for use in surgery for drilling holes in bones comprising a tool socket having an elongated sleeve for shielding soft tissue from contact with a drill operating through said socket, teeth on said sleeve for anchoring to a bone a direction finder connected to said socket and having an axis at a predetermined angle to the axis of the tool socket for indicating the axial alignment of the tool socket and an elongated handle connected to the direction finder and tool socket whereby the socket and direction finder may be held in a predetermined orientation between a radiation source and a radiation receiver.

* * * * *

UNITED STATES PATENT AND TRADEMARK OFFICE
CERTIFICATE OF CORRECTION

PATENT NO. : 4,803,976
DATED : February 14, 1989
INVENTOR(S) : R. Frigg, P. Gisin, S. Perren, U. Jenny and G. Ritter It is certified that error appears in the above—identified patent and that said Letters Patent is hereby corrected as shown below:

Title page, Assignee designation, delete "Synthes, Paoli, Pa." and substitute therefor --Synthes (U.S.A.), Paoli, Pa.--.

Column 3, line 26, after "90°", delete --L--.

Signed and Sealed this

Nineteenth Day of September, 1989

Attest:

DONALD J. QUIGG

Attesting Officer     Commissioner of Patents and Trademarks